United States Patent [19]

Vaughan, III et al.

[11] 4,227,246

[45] Oct. 7, 1980

[54] MULTI-PARAMETER MEASUREMENT SYSTEM FOR FLUIDS

[76] Inventors: Warren T. Vaughan, III; Gordon MacDonnell, both of San Francisco, Calif.

[21] Appl. No.: 957,866

[22] Filed: Nov. 6, 1978

Related U.S. Application Data

[63] Continuation of Ser. No. 796,738, May 13, 1978, abandoned.

[51] Int. Cl.² .............................................. G06F 15/10
[52] U.S. Cl. .................................... 364/571; 364/510
[58] Field of Search ............... 364/571, 509, 510, 421, 364/422, 423; 250/256, 258, 262; 73/196, 194 R, 194 VS, 194 G, 194 E; 340/15.5 DP, 15.5 VD; 324/1, 2, 4-8

[56] References Cited

U.S. PATENT DOCUMENTS

| | | | |
|---|---|---|---|
| 3,479,580 | 11/1969 | Hottel, Jr. ................................ | 324/1 |
| 3,878,374 | 4/1975 | Schlatter .......................... | 364/509 X |
| 4,031,780 | 6/1977 | Paap et al. ....................... | 364/510 X |
| 4,055,763 | 10/1977 | Antkiw ............................ | 364/422 X |
| 4,101,866 | 7/1978 | Ruehle ............................ | 364/421 X |
| 4,118,780 | 10/1978 | Hirano ................................. | 364/510 |

*Primary Examiner*—Edward J. Wise
*Attorney, Agent, or Firm*—Phillips, Moore, Weissenberger, Lempio & Majestic

[57] ABSTRACT

There is provided a multi-parameter, self-contained, programmable, microcomputer-controlled monitoring system for the measurement of physical and chemical properties of water and other fluids. Data are stored within a sensor packge according to a chosen format and schedule. Oceanographic and limnological data are thus gathered without need of umbilical power and/or data links to external devices. A programming and interpreting device provides analytic interface with the sensor packge for logic input and data readout. Program-controlled analog/digital conversion yields constants for calibration of sensors which leads to freedom from measurement drift as well as great versatility and accuracy.

11 Claims, 2 Drawing Figures

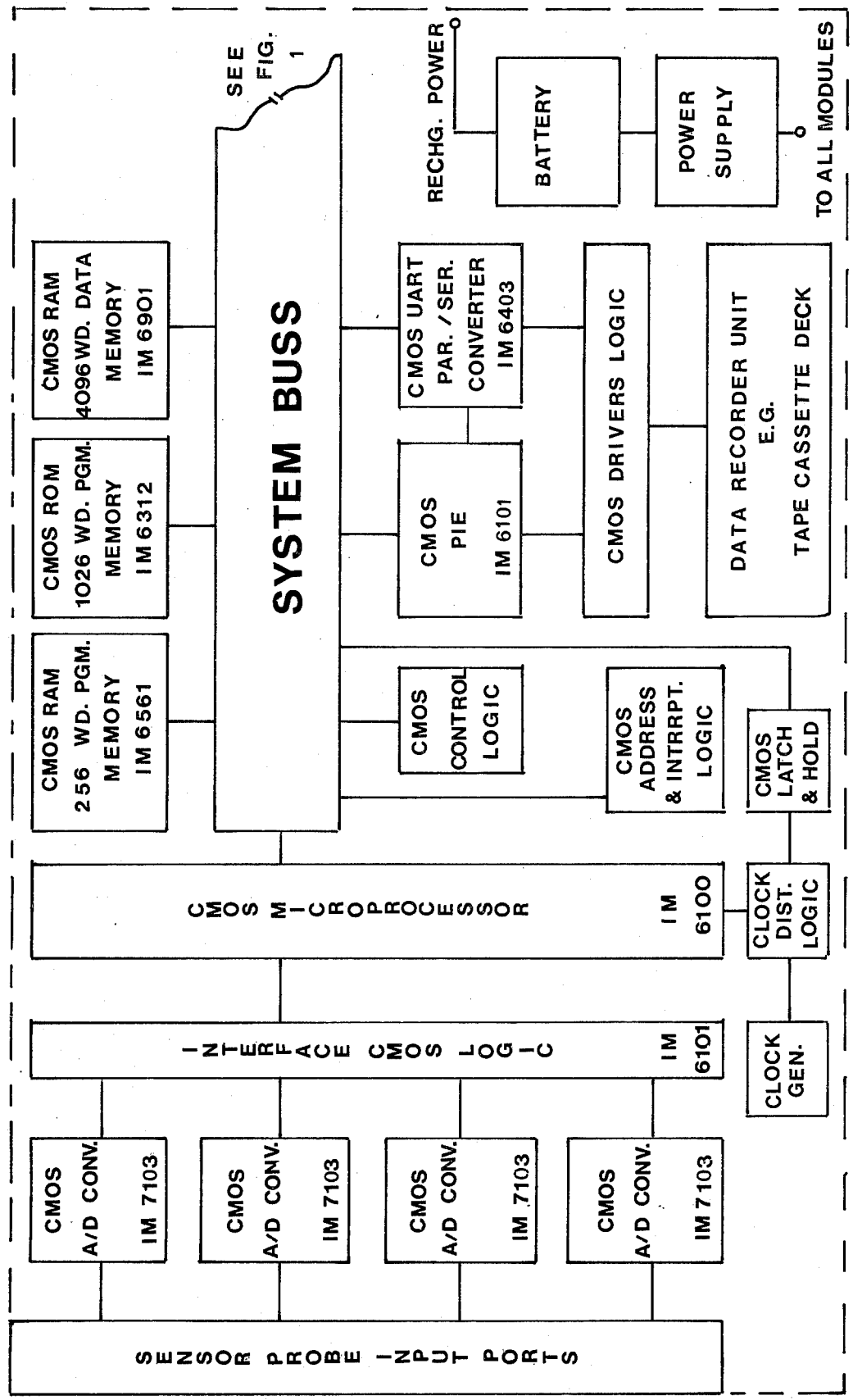

MULTI-PARAMETER MEASUREMENT SYSTEM FOR FLUIDS

This is a continuation, of Ser. No. 796,738, filed May 13, 1978, now abandoned.

BACKGROUND OF THE INVENTION

The invention described herein relates in general to the measurement and the analysis of physical and chemical properties of water and other fluids. More particularly, the subject invention is a system for the synchronous collection of selected fluid-related data and for management of these data, including storage and display of information.

Information as to the constituency and character of fluids, particularly water, is necessary in many applications such as for oceanographic and limnological research, for pollution control and monitoring, for industrial process and quality control, for acquaculture and fishery programs, and as an educational tool for predicted learning projects in schools. Present measurement and analytical devices are either too cumbersome, complex and expensive, or they are unsophisticated and limited in scope, lacking necessary accuracy and reliability. Heretofore, fluid measurement devices have not provided a simple, inexpensive, accurate, and self-contained means of acquiring and storing data of and within a fluid environment.

The present invention has overcome the disadvantages of prior fluid measurement and analytical methods and provides a highly versatile, accurate, self-calibrating and programmable system which may be used independent of external power and control requirements. The non-complex operation of the instant invention enables the collection of data by operators unskilled in the science of chemical and physical analysis. The subject invention stores accumulated information within an immersed Probe Control Unit during soundings. Data need not, therefore, be immediately transmitted to a surface of external reading device, but may be accussed later by use of a compatible Interpreter Unit, or data cassettes may be withdrawn and shipped to an information processing center away from the field.

Accordingly, it is an object of the subject invention to provide a simple, low-cost, multi-function, programmable, microcomputer-controlled fluids analysis system.

It is a further object of the subject invention to provide a self-contained, automated system to better meet the needs of all individuals and entities involved in the measurement and analysis of fluids.

DESCRIPTION OF DRAWINGS

FIG. 2 is a schematic block diagram of the underwater (or fluid-immersed) Probe Control Unit.

SUMMARY OF THE INVENTION

Figure 1:
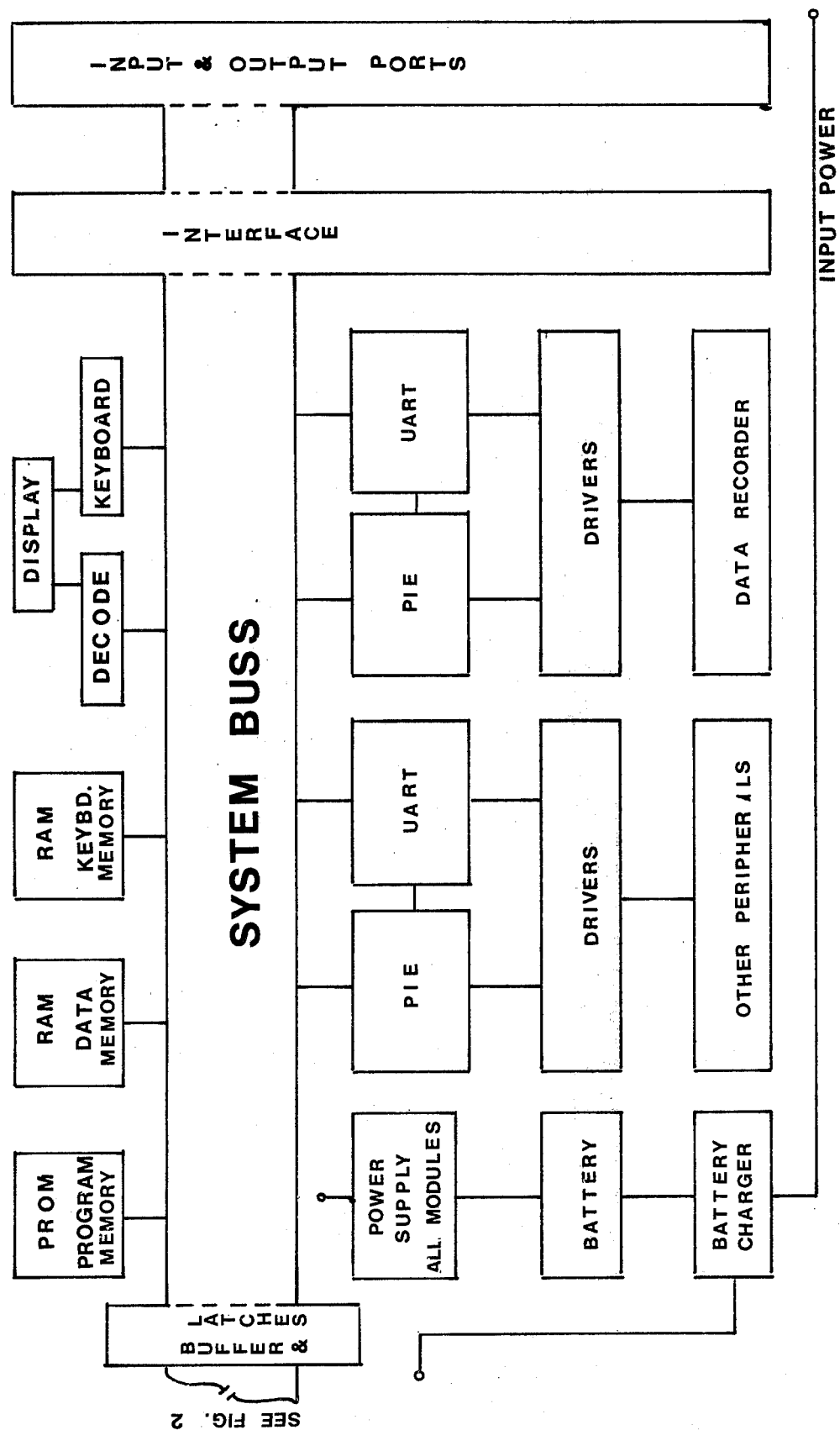
FIG. 1 is a schematic block diagram of the surface Interpreter Unit.

The surface Interpreter Unit provides for programming of the underwater Probe Control Unit prior to immersion. The Interpreter Unit controls the specific measurements desired for each sounding. The system can be programmed for triggering at specific depths, times, temperatures, etc., or any combination of chosen parameters. The Interpreter Unit includes:

1. A housing
2. A keyboard
3. A program memory
4. A data memory
5. Interface circuitry
6. A power supply, rechargeable batteries, and a battery charger
7. A visual readout
8. A data buss
9. A control buss
10. An address buss
11. A buffer and latches
12. A keyboard memory
13. CMOS parallel interface elements
14. CMOS parallel/serial converters
15. A data recorder unit The underwater Probe Control Unit is self-contained, independent of umbilical power and/or data links of the surface or a mother-ship, and independent of sonic, radio or other telemetering means. The Probe Control Unit includes:

1. A housing
2. Probes chosen for selected parameters
3. CMOS analog/digital converters and interfaces
4. A CMOS microprocessor central processing unit
5. A CMOS static program memory, counters, and buffers
6. A real-time clock, generator, and counter
7. A CMOS data storage memory
8. CMOS control logic for address decoding and interupt priority
9. A power supply and rechargeable batteries
10. A data buss
11. A control buss
12. A data recorder unit
13. CMOS parallel interface elements
14. CMOS parallel/serial converters
15. CMOS drivers The resultant microcomputer uses thousands of programmed instructions and stored table entries to perform hundreds of essentially bit-parallel, word-serial, sequential operations of digital data in pre-programmed order. These logical operations accomplish functions which include control of measurement processes, interfacing, linearization of probe data, determination of calibration constants, data management, shifting converting, inverting, merging, computation, incrementing, deincrementing, self-checking of reference memory, etc.

This system can modify functions, times, triggering options, parameters, and sequences of parameters to be measured and recorded, depending upon the results of other parameters measured, all according to predetermined values and standards. Pre-programmed by professionals, the system may then be operated by laymen, as no operator monitoring or intervention is required. This feature eliminates unwanted variables due to operator or environmental conditions and greatly reduces field operation expense, while at the same time improving reliability, flexibility, productivity, and ultimate accuracy.

Gathered data are recorded on a digital tape cassette within the Probe Control Unit and may be recalled for immediate readout at the Interpreter Unit following soundings. Data may then be transmitted by radio or wire, entered directly into a ship-board or other computer, or forwarded to a remote agency equipped to collate the data as part of a specific project. This highly versatile and adaptable fluids measurement and analysis system monitors a selected number of the following parameters during soundings:
1. Time
2. Depth by Pressure and Salinity
3. Temperature
4. Conductivity and Salinity
5. Dissolved Oxygen
6. pH
7. Current Velocity
8. Current Direction
9. Turbidity/Irradiance
10. Oil and Grease
11. Suspended Solids
12. Chemicals Oxygen Demand
13. Coliform Bacteria
14. Lead
15. Mercury
16. Cadmium
17. Nickle
18. Arsenic
19. Plant Nutrients
20. Synthetic Organics
21. Sunlight Attenuation
22. Ion Metering
23. Fluorescent Chlorophyll
24. Residual Chlorine Many of the parameters to be measured involve technologies wherein analog probes experience significant degradation and drift, thus making frequent recalibration essential. Analog probes made for use in the existing systems are available for many of the above parameters, and are adaptable for use with the digital system of the subject invention. This system provides microcomputer-controlled analog/digital conversion and interfacing, performs the functions of log amplifiers and multiplying networks to linearize probe output, and determines constants for recalibration. Freedom from drift, greater versatility, and higher accuracy are employed logically to replace nonlinear circuits and much of the hardware required by prior art in the use of analog probes.

Many of the complex functions in sensing, control, data processing, recording and display that in prior art have been performed with complex and expensive hardware are accomplished largely by the operating software and programming of the subject invention. Prior art has primarily involved hardware and circuitry rather than input interface and control, computation, and programming techniques. With the subject system, innovative programmers will redesign the system to perform additional measurements and analyses by modifying the software, and by assigning even more complexity to the software.

What is claimed is:

1. A self-contained, independent probe control unit for monitoring at least one parameter of a fluid, comprising:
   (a) a housing immersible in the fluid;
   (b) means, connected to said housing, for sensing the parameter and providing output parameter data;
   (c) programmable, microcomputer control means, supported in said housing, for processing the output data from said sensing meas; and
   (d) means, supported in said housing, for storing the processed data.

2. A probe control unit according to claim 1, wherein said control means includes means for automatically reprogramming said control means in response to the output data from said sensing means.

3. A probe control unit according to claim 1, wherein said control means includes means for independently operating said sensing means, said control means and said storing means from the time said housing is immersed in the fluid to the time said housing is recovered for access to the stored data.

4. A probe control unit according to claim 1, wherein said control means and said storing means include means for gathering and storing data independent of imbilical power or data links from above the surface of the fluid.

5. A probe control unit according to claim 1, further including batteries stored in said housing for supplying power for the unit.

6. A probe control unit according to claim 1, wherein said control means includes means for automatically calibrating said sensing means during unit monitoring.

7. A probe control unit according to claim 1, wherein said control means includes means for eliminating drift and degradation of the output data from said sensing means.

8. A probe control unit according to clam 1, wherein said sensing means includes an analog probe.

9. A probe control unit according to claim 1, wherein said control means includes means for computing information based on the output data from said sensing means, said storing means including means for storing the computed information.

10. A probe control unit according to claim 1, wherein said control means includes software for measuring and analyzing the output data from said sensing means.

11. A system for monitoring at least one parameter of a fluid, comprising:
   (a) a self-contained, independent probe control unit for monitoring at least one parameter of a fluid, including
      (i) a housing immersible in the fluid;
      (ii) means, connected to said housing, for sensing the parameter and providing output parameter data;
      (iii) programmable, microcomputer control means, supported in said housing, for processing the output data from said sensing means; and
      (iv) means, supported in said housing for storing the processed data; and
   (b) an interpreter unit locatable above the surface of the fluid and including means for programming said control means to initiate processing of the data under a predetermined condition, said probe control unit and said interpreter unit being independent of each other during system monitoring.

* * * * *

UNITED STATES PATENT AND TRADEMARK OFFICE
CERTIFICATE OF CORRECTION

PATENT NO. : 4,227,246

DATED : October 7, 1980

INVENTOR(S) : Warren T. Vaughan, III; and Gordon MacDonnell

It is certified that error appears in the above—identified patent and that said Letters Patent is hereby corrected as shown below:

Abstract, line 5, after "sensor" and before "according", it should read --package--.

Column 1, line 41, after "be", it should read --accessed--.

Column 2, line 57, after "operator" and before "or" insert --technique--.

Column 4, line 3, after "sensing" and before "and" it should read --means--.

Signed and Sealed this

Third Day of March 1981

[SEAL]

*Attest:*

RENE D. TEGTMEYER

*Attesting Officer*  Acting Commissioner of Patents and Trademarks